US008903147B2

(12) United States Patent
Iwasaki

(10) Patent No.: US 8,903,147 B2
(45) Date of Patent: Dec. 2, 2014

(54) MEDICAL REPORT GENERATION APPARATUS, METHOD AND PROGRAM

(75) Inventor: Taiji Iwasaki, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 281 days.

(21) Appl. No.: 13/434,242

(22) Filed: Mar. 29, 2012

(65) Prior Publication Data

US 2012/0250961 A1 Oct. 4, 2012

(30) Foreign Application Priority Data

Mar. 30, 2011 (JP) .................... 2011-073808

(51) Int. Cl.
*G06T 7/00* (2006.01)
*G06F 19/00* (2011.01)
*A61B 5/00* (2006.01)

(52) U.S. Cl.
CPC .......... *G06F 19/321* (2013.01); *G06F 19/3487* (2013.01); *G06F 19/322* (2013.01); *G06F 19/3406* (2013.01); *G06F 19/3443* (2013.01); *G06F 19/345* (2013.01); *A61B 5/748* (2013.01); *A61B 2576/00* (2013.01)
USPC .......................................... 382/128; 382/131

(58) Field of Classification Search
None
See application file for complete search history.

(56) References Cited

U.S. PATENT DOCUMENTS

| 5,940,527 | A | 8/1999 | Takeo |
| 2002/0181754 | A1 | 12/2002 | Masumoto et al. |
| 2003/0095692 | A1 | 5/2003 | Mundy et al. |
| 2005/0010100 | A1 | 1/2005 | Hornegger et al. |
| 2009/0087048 | A1* | 4/2009 | Takahashi ............... 382/128 |
| 2009/0257550 | A1 | 10/2009 | Moriya |
| 2012/0081362 | A1* | 4/2012 | Kiraly et al. ............ 345/419 |

FOREIGN PATENT DOCUMENTS

| JP | 8007080 A | 1/1996 |
| JP | 8-215183 A | 8/1996 |
| JP | 2001-137230 A | 5/2001 |
| JP | 2001-283191 A | 10/2001 |
| JP | 2003-271924 A | 9/2003 |
| JP | 2004-141612 A | 5/2004 |
| JP | 2005-327302 A | 11/2005 |
| JP | 2008-43564 A | 2/2008 |
| JP | 2008132019 A | 6/2008 |
| JP | 2008-253293 A | 10/2008 |
| JP | 2009223595 A | 10/2009 |
| JP | 2009247817 A | 10/2009 |
| JP | 2010-182179 A | 8/2012 |

OTHER PUBLICATIONS

Japanese Office Action Application No. 2011073808; Jan. 15, 2013.

(Continued)

*Primary Examiner* — Jon Chang
(74) *Attorney, Agent, or Firm* — Sughrue Mion, PLLC

(57) ABSTRACT

A medical report generation apparatus includes a key image selection unit that selects, as a key image representing a diagnostic characteristic feature, a slice image generated based on three-dimensional medical image data obtained by imaging a subject, a selected position input unit that inputs a selected position in the key image, a supplementary image determination unit that determines, based on the key image and the selected position, a slice image that includes the selected position and represents a cross section different from a cross section represented by the key image, as a supplementary image, in the three-dimensional medical image data, and a medical report generation unit that generates a medical report including the key image and information for identifying the supplementary image.

9 Claims, 5 Drawing Sheets

(56) References Cited

OTHER PUBLICATIONS

Hiroshi Fujita et al, "Intelligent Computer-Aided Diagnosis Based on Normal Structure Recognition of Human Body", Grant-in-Aid for Scientific Research granted by the Ministry of Education, Culture, Sports, Science and Technology (MEXT), Study in Specific Field, Proceedings of 4th Symposium, 2007, pp. 55-60.

K. Kubota et al., "Evaluation of Computer-Aided Diagnosis System for Lung Cancer Based on Helical CT Images", Institute of Electronics, Information and Communication Engineers (IEICE), 2001, pp. 41-46.

Shoji Kido et al., "Intelligent CAD for Diffuse Lung Diseases", 2007, pp. 45-54.

Y. Wakida et al., "Liver Cancer Detection based on Temporal Density Feature from Abdominal Dynamic X-ray CT Images", Proceedings of Japan Society of Computer-Aided Diagnosis of Medical Images, 2007, vol. 10, No. 1.

* cited by examiner

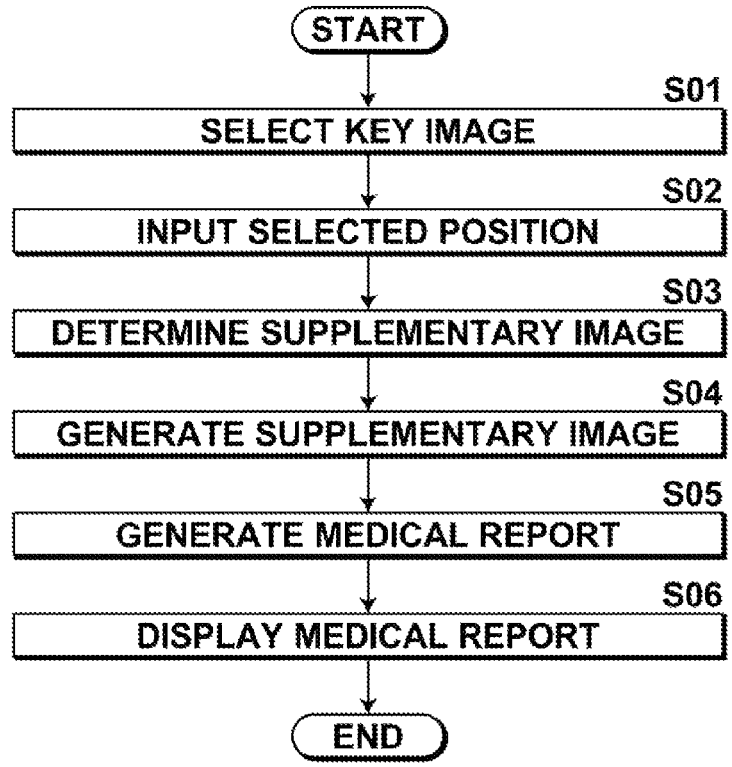
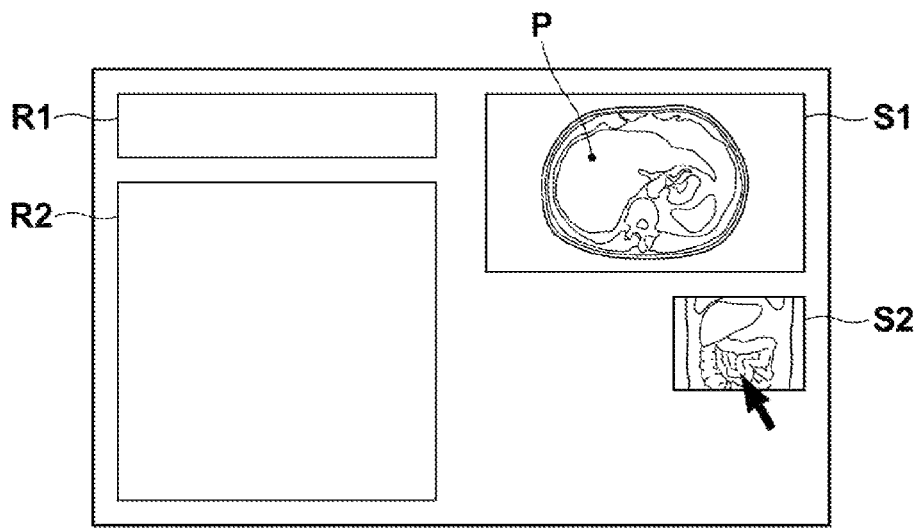

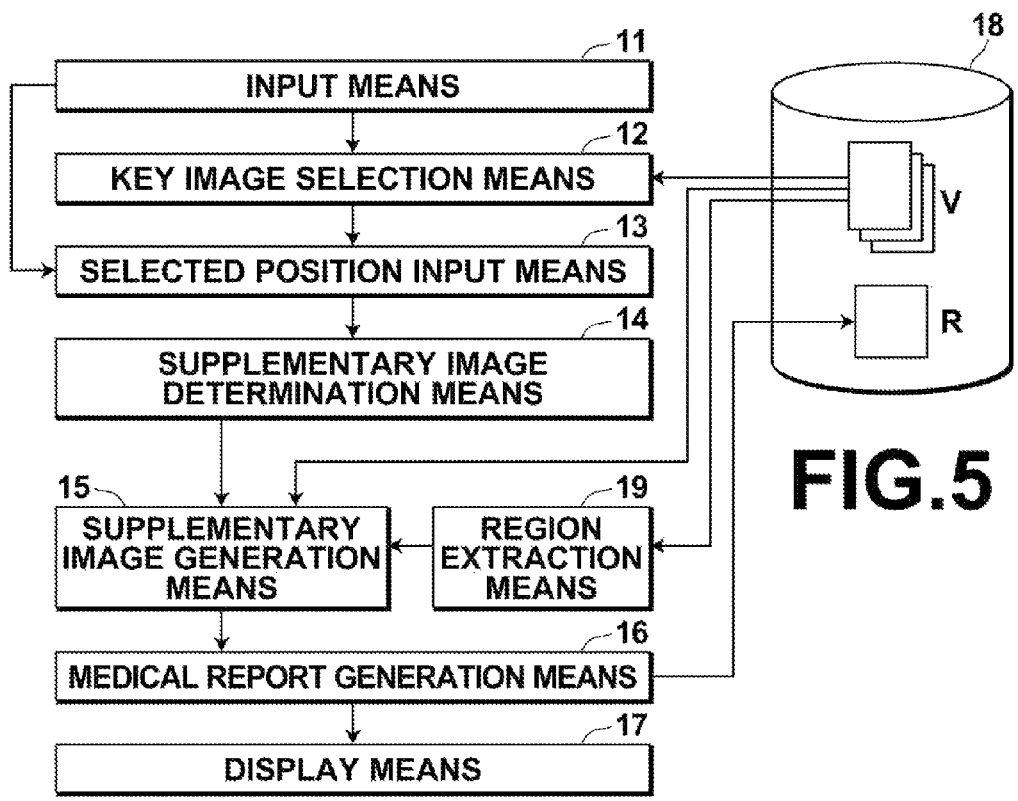
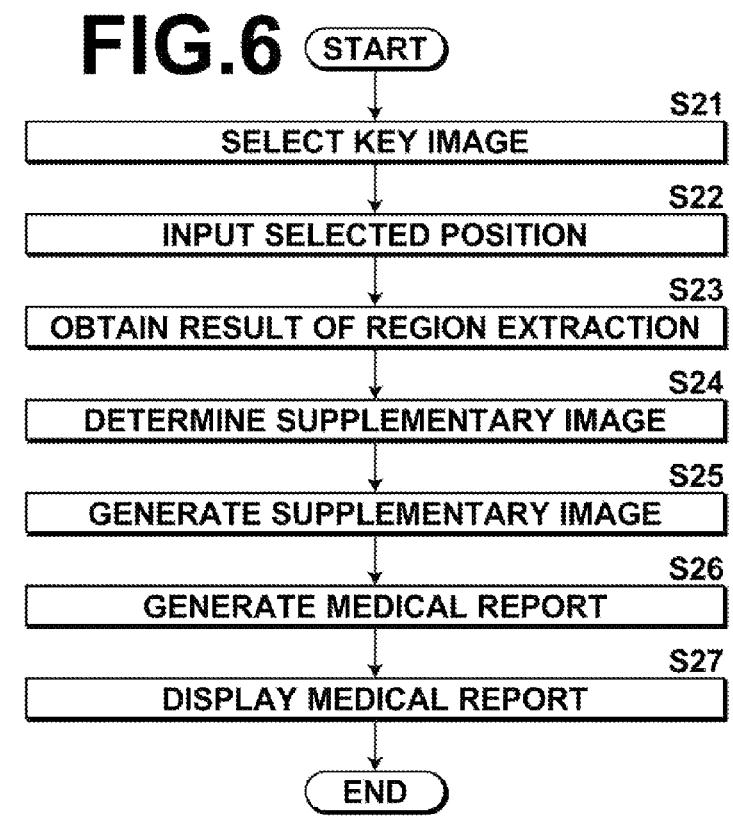

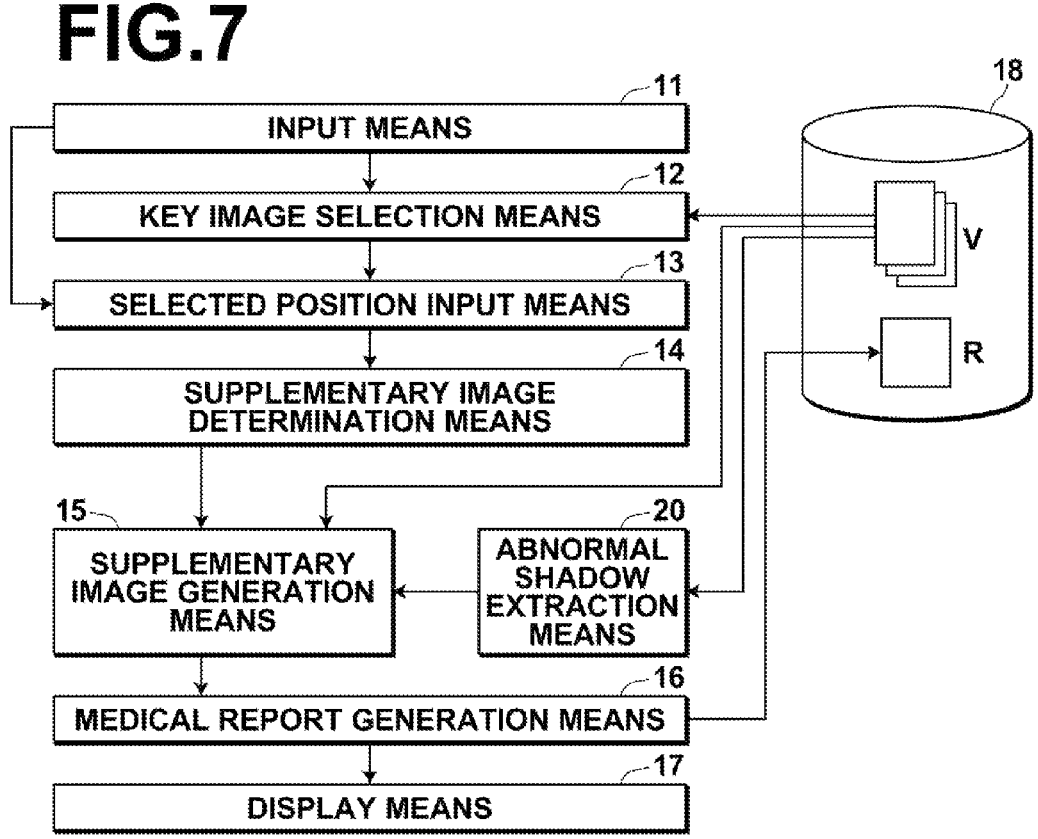

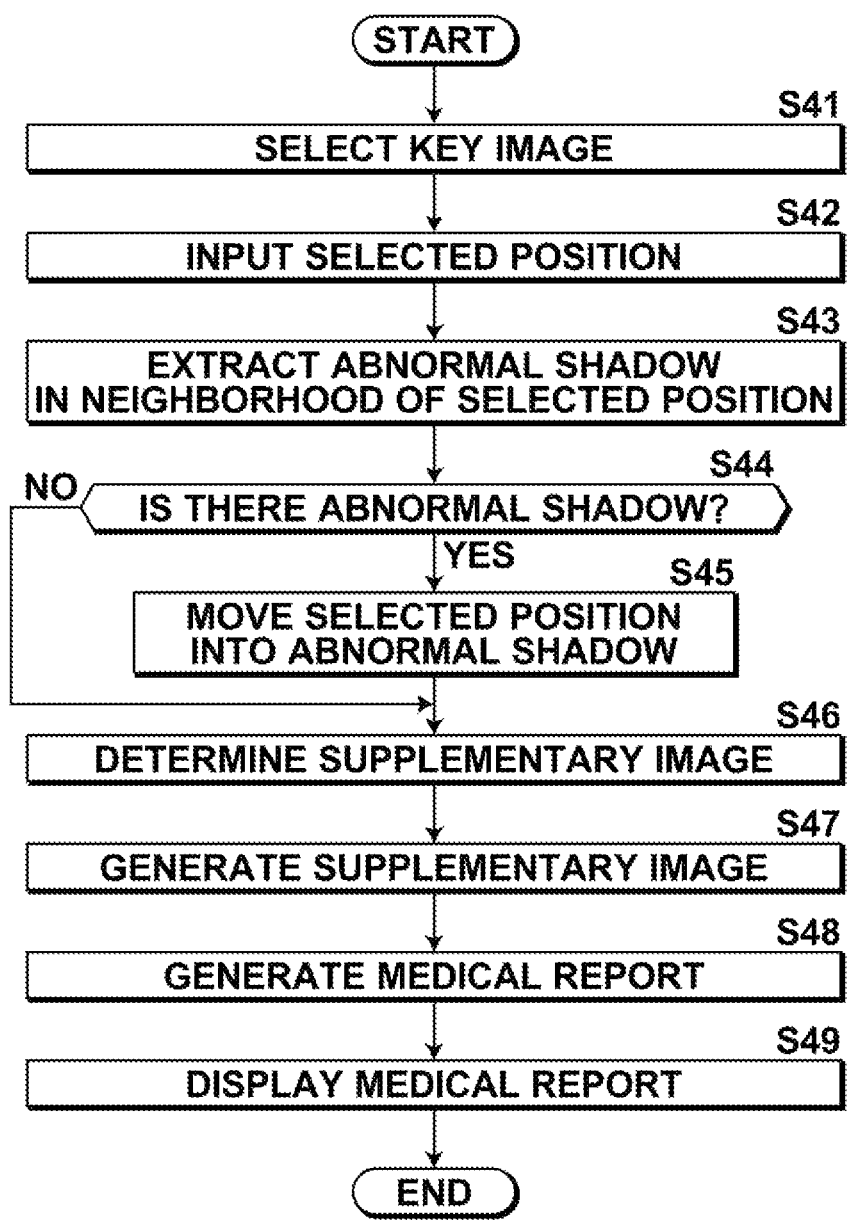

MEDICAL REPORT GENERATION APPARATUS, METHOD AND PROGRAM

BACKGROUND OF THE INVENTION

1. Field of the Invention

The present invention relates to a medical report generation apparatus, a medical report generation method and a medical report generation program for generating a medical report about image-based diagnosis of a patient.

2. Description of the Related Art

In image-based diagnosis in medical fields, a person in charge of generating a medical report reads and interprets a medical image obtained by imaging a patient, and generates the medical report that describes position information about a region of interest judged to be important for diagnosis, and to which a key image including the region of interest is attached. Further, a doctor or the like checks the generated medical report to diagnose the patient.

However, when only the key image attached to the medical report and the position information about the region of interest described in the medical report are provided, the information is insufficient for a doctor or the like in some cases to diagnose a patient while accurately recognizing the region of interest, such as the position and the size of a diseased part or the like. In such cases, the doctor or the like needs to obtain a supplementary image by manually retrieving an image in which the region of interest is recognizable from images of the patient obtained by imaging. That may impose time and work on the doctor or the like.

Japanese Unexamined Patent Publication No. 2010-182179 (Patent Document 1) discloses an apparatus that makes a doctor easily recognize the location of a lesion by generating and displaying a lesion location image representing the location of the lesion in a schematic diagram. The lesion location image is generated based on report data including information about the position of the lesion and schematic image data representing the schematic diagram illustrating the structure of an anatomical region in which the lesion is present.

Japanese Unexamined Patent Publication No. 2005-327302 (Patent Document 2) discloses an apparatus that displays a key image, which is a key for image-based diagnosis, and an image related to the key image in a medical report when a user displays and checks report data. The image related to the key image is generated from a picture archiving and communication system (PACS), based on report data generated by attaching the key image and an image processing parameter set necessary to generate the key image to the medical report, by using the image processing parameter set necessary to generate the key image or an image processing parameter set obtained by modifying the image processing parameter set necessary to generate the key image.

However, the method disclosed in Patent Document 1 indicates the location of a lesion in the schematic diagram. Therefore, the position of an actual region, skeleton or the like of a patient and an anatomical position in the schematic diagram do not sufficiently match with other. Hence, comparison has been difficult in some cases. Further, in the method disclosed in Patent Document 2, when a user displays and checks the medical report, the user needs to specify an image to generate and display the image related to the key image. Therefore, there has been a problem that selection of the image related to the key image is not easy for a user who is not used to an operation for appropriately changing an image processing parameter set and an operation for selecting the image related to the key image.

SUMMARY OF THE INVENTION

In view of the foregoing circumstances, the present invention provides a medical report generation apparatus, method and program in which a supplementary image that can assist a user in understanding a key image, which has been judged to be important for diagnosis, is easily and appropriately selected when a medical report to which the key image is attached is generated.

A medical report generation apparatus of the present invention is a medical report generation apparatus comprising:

a key image selection means that selects, as a key image representing a diagnostic characteristic feature, a slice image generated based on three-dimensional medical image data obtained by imaging a subject;

a selected position input means that inputs a selected position in the key image;

a supplementary image determination means that determines, based on the key image and the selected position, a slice image that includes the selected position and represents a cross section (slice plane) different from a cross section represented by the key image, as a supplementary image in the three-dimensional medical image data; and a medical report generation means that generates a medical report including the key image and information for identifying the supplementary image.

A medical report generation method of the present invention is a medical report generation method comprising the steps of:

selecting, as a key image representing a diagnostic characteristic feature, a slice image generated based on three-dimensional medical image data obtained by imaging a subject;

inputting a selected position in the key image;

determining, based on the key image and the selected position, a slice image that includes the selected position and represents a cross section different from a cross section represented by the key image, as a supplementary image in the three-dimensional medical image data; and generating a medical report including the key image and information for identifying the supplementary image.

A medical report generation program of the present invention is a program for causing a computer to function as:

a key image selection means that selects, as a key image representing a diagnostic characteristic feature, a slice image generated based on three-dimensional medical image data obtained by imaging a subject;

a selected position input means that inputs a selected position in the key image;

a supplementary image determination means that determines, based on the key image and the selected position, a slice image that includes the selected position and represents a cross section different from a cross section represented by the key image, as a supplementary image in the three-dimensional medical image data; and a medical report generation means that generates a medical report including the key image and information for identifying the supplementary image.

The three-dimensional medical image data may be obtained by imaging by an arbitrary imaging apparatus as long as an arbitrary cross section is reconstructible therefrom. Representative examples of the three-dimensional medical image data are volume data composed of three-dimensionally-arranged voxels, and which are obtained by imaging by a CT apparatus, an MRI apparatus, and the like.

A slice image represented by using an arbitrary slice generation method may be used as the key image. For example, in a coordinate space in which the body axis direction of a subject is z-axis direction and a direction toward the front of the subject is y-axis direction, an axial image, a coronal image, a sagittal image, and the like may be used. The axial image is a slice image orthogonal to z-axis, and the coronal image is a slice image orthogonal to y-axis, and the sagittal image is a slice image orthogonal to x-axis. Alternatively, an arbitrary slice image obtained by an MPR (Multi-Planner Reconstruction) method, an MPVR (MultiProjection Volume Reconstruction) method, or the like may be used.

The supplementary image may be any kind of slice image as long as the slice image represents a cross section that is different from a cross section represented by the key image. It is desirable that the key image and the supplementary image do not represent the same plane so that a user can refer to a sufficiently large range by using the key image and the supplementary image. For that purpose, it is desirable that an angle between a normal to a plane including the key image and a normal to a plane including the supplementary image is greater than a predetermined degree. Further, it is desirable that the supplementary image represents a cross section in such a manner that the position of the cross section in the whole subject is easily recognizable even by a clinical doctor (a doctor in a clinical department) who is not used to image reading (interpretation of images). It is desirable that the supplementary image is an image that is often used in medical treatment, for example, such as an axial image, a coronal image, and a sagittal image. For example, it is desirable that the key image is an axial image, and the supplementary image is a coronal image. Alternatively, arbitrary slice images obtained by the MPR method or the MPVR method may be used.

Further, the medical report including information for identifying the supplementary image may include the supplementary image itself. Alternatively, the medical report may include only information for identifying the supplementary image, and based on which the supplementary image can be generated.

Further, it is desirable that the supplementary image determination means of the present invention determines the supplementary image in such a manner that the inclination of a cross section represented by the supplementary image differs based on the selected position. For example, it is desirable that the medical report generation apparatus of the present invention further includes a region extraction means that extracts a region including the input selected position from the three-dimensional medical image data, and that the supplementary image determination means determines the supplementary image in such a manner that the inclination of the cross section represented by the supplementary image differs based on the extracted region.

In the aforementioned case, it is more desirable that the supplementary image determination means determines a sagittal image as the supplementary image when the extracted region is curved toward the front direction (anterior direction) of the subject and the key image is not a sagittal image.

It is desirable that the medical report generation apparatus of the present invention further includes an abnormal shadow extraction means that extracts an abnormal shadow within a predetermined neighborhood range from the selected position, and that the supplementary image determination means determines the supplementary image by moving the selected position into the extracted abnormal shadow.

Further, the supplementary image determination means of the present invention may determine an MPVR (multiprojection volume reconstruction) image, as the supplementary image.

A medical report generation apparatus of the present invention may further include an image generation means that generates the supplementary image based on the information for identifying the supplementary image, and a display means that displays the medical report including the generated supplementary image.

According to a medical report generation apparatus, method and program of the present invention, a slice image generated based on three-dimensional medical image data obtained by imaging a subject is selected, as a key image representing a diagnostic characteristic feature, and a selected position in the key image is input, and a slice image that includes the selected position and represents a cross section different from a cross section represented by the key image is determined, as a supplementary image, in the three-dimensional medical image data based on the key image and the selected position, and a medical report including the key image and information for identifying the supplementary image is generated. Therefore, it is possible to easily generate the supplementary image representing the selected position by a different cross section, and to efficiently generate a medical report. Further, since a doctor or the like who uses the medical report for diagnosis can easily refer to the supplementary image, the doctor or the like can easily understand the medical report.

Note that the program of the present invention may be provided being recorded on a computer readable medium. Those who are skilled in the art would know that computer readable media are not limited to any specific type of device, and include, but are not limited to: floppy disks, CD's, RAM'S, ROM's, hard disks, magnetic tapes, and internet downloads, in which computer instructions can be stored and/or transmitted. Transmission of the computer instructions through a network or through wireless transmission means is also within the scope of this invention. Additionally, computer instructions include, but are not limited to: source, object and executable code, and can be in any language including higher level languages, assembly language, and machine language.

BRIEF DESCRIPTION OF THE DRAWINGS

FIG. 3 is a flowchart illustrating a flow of medical report generation processing in the first embodiment of the present invention;

FIG. 4 is a diagram for explaining an example of a medical report generated in the first embodiment;

FIG. 5 is a functional block diagram of a medical report generation apparatus according to a second embodiment of the present invention;

FIG. 6 is a flowchart illustrating a flow of medical report generation processing in the second embodiment of the present invention;

FIG. 7 is a functional block diagram of a medical report generation apparatus according to a third embodiment of the present invention; and FIG. 8 is a flowchart illustrating a flow of medical report generation processing in the third embodiment of the present invention.

DESCRIPTION OF THE PREFERRED EMBODIMENTS

Figure 1:
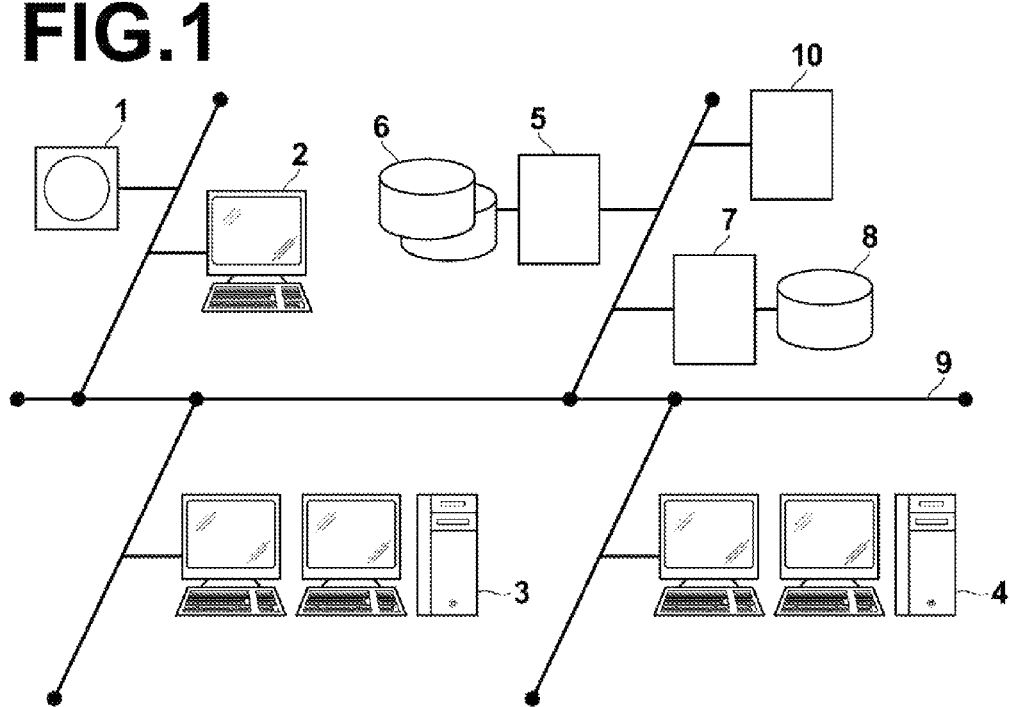
FIG. 1 is a diagram illustrating a medical report generation network according to a first embodiment of the present invention.

Hereinafter, embodiments of the present invention will be described with reference to drawings. In the specification of the present application, the same reference numerals will be assigned to the same composition elements, and the explanations of the same composition elements will be omitted. FIG. 1 is a schematic diagram illustrating the configuration of a medical information system into which a medical report generation apparatus according to an embodiment of the present invention has been introduced. This system is used to image an examination target region of a subject (patient) based on an examination order from a doctor in a clinical department who uses a known ordering system, and to store obtained images. Further, the system is used by a radiologist, who reads images in a radiology department, to read the images obtained by imaging and to generate a medical report. Further, the system is used by the doctor in the clinical department, who has requested examination, to retrieve the medical report and to observe, in detail, the images that have been a target of reading by the radiologist. As illustrated in FIG. 1, the medical information system includes an imaging apparatus (modality) 1 for obtaining medical images, a workstation (QA-WS) 2 for checking image qualities, a workstation 3 for a radiology department, a workstation 4 for a clinical department, an image information management server 5, an image information database 6, a medical report server 7, a medical report database 8, and an information management server 10, which are connected to each other through a network 9 in such a manner that they can communicate with each other. Each device is controlled by a program installed from a recording medium, such as a CD-ROM. Alternatively, the program may be installed after being downloaded from a recording device of a server connected to the system through a network, such as the Internet.

The modality 1 includes an apparatus that generates image data representing an examination target region of a subject by imaging the region, and that outputs the image data, as image information, after attaching supplementary information defined by DICOM standard to the image data. Specific examples of the modality 1 are CT, MR, PET, and ultrasonic imaging apparatuses, an X-ray radiography apparatus using a flat panel X-ray detector (FPD), and the like. Hereinafter, a pair of image data representing a subject and supplementary information about the image data will be referred to as "image information". Specifically, the "image information" includes text information about the image.

The QA-WS 2 includes a general-purpose processing apparatus (computer), one or two high-definition displays, and an input device, such as a keyboard and a mouse. Further, software for assisting an examination specialist in examination operations has been installed in the processing apparatus. The QA-WS 2 receives image information based on DICOM from the modality 1, and displays image data and the content of supplementary information included in the received image information on a display screen by functions realized by executing the software program. Accordingly, the QA-WS 2 prompts the examination specialist to check the image information. After the examination specialist has checked the image information, the image information is transferred to the image information management server 5 through the network 9. Further, registration of the image information in the image information database 6 is requested.

The workstation 3 for the radiology department is a computer used by a doctor (radiologist), who interprets images and performs image-based diagnosis, in the radiology department to read the images and to generate a medical report. The workstation 3 for the radiology department has known hardware configuration including a CPU, a main storage device, an auxiliary storage device, an input/output interface, a communication interface, an input device, a display device, a data bus, and the like. Further, a known operation system and the like have been installed in the workstation 3 for the radiology department. The workstation 3 for the radiology department includes a display device and one or two high definition displays. In this apparatus, each processing is performed by execution of respective software programs for each processing. Specifically, the processing includes requesting the image information management server 5 to retrieve an image, displaying the image received from the image information management server 5, automatically detecting a region that is likely to be a lesion in the image and displaying the detected region in an emphasized manner, assisting a user in generation of a medical report, requesting the medical report server 7 to register or retrieve the medical report, displaying the medical report received from the medical report server 7, requesting the information management server 10 to register or retrieve patient's information and the like, displaying the patient's information received from the information management server 10, and the like. The medical report generation apparatus of the present invention is installed in the workstation 4 for a clinical department, and a software program for diagnosis-assistance processing disclosed in the specification of the present application is installed in the apparatus. The medical report generation processing disclosed in the specification of the present application is performed by execution of the software program, as will be described later.

The workstation 4 for a clinical department is a computer used by a doctor in the clinical department to observe an image in detail, to retrieve a medical report, to retrieve an electronic chart or to input data in the electronic chart, and the like. The workstation 4 for a clinical department has known hardware configuration including a CPU, a main storage device, an auxiliary storage device, an input/output interface, a communication interface, an input device, a display device, a data bus, and the like. Further, a known operation system and the like have been installed in the workstation 4 for a clinical department. The workstation 4 for a clinical department includes a display device and one or two high definition displays. In this apparatus, each processing is performed by execution of a software program for each processing. Specifically, the processing includes requesting the image information management server 5 to retrieve an image, displaying the image received from the image information management server 5, automatically detecting a region that is likely to be a lesion in the image and displaying the detected region in an emphasized manner, requesting the medical report server 7 to retrieve the medical report, displaying the medical report received from the medical report server 7, requesting the information management server 10 to register or retrieve patient's information and the like, displaying the patient's information and the like received from the information management server 10, and the like.

The image information management server 5 is a general-purpose computer with a relatively high processing performance in which a software program providing a function of a database management system (DataBase Management System: DBMS) has been installed. The image information management server 5 is a so-called PACS (Picture Archiving and Communication Systems) server. The image information management server 5 includes a large capacity storage in which the image information database 6 is structured. This storage may be a large-capacity hard disk connected to the image information management server 5 through a data bus. Alternatively, the storage may be an NAS (Network Attached Storage) connected to the network 9 or a disk device connected to an SAN (Storage Area Network).

In the image information database 6, image data representing an image of a subject and supplementary information are registered. The supplementary information may include, for example, an image ID for identifying each image, a patient's ID for identifying a subject, an examination ID for identifying an examination, a unique ID (UID) allocated to each image information, a date of examination on which the image information has been generated, the time of examination, the kind of a modality used in the examination to obtain the image information, patient's information, such as a patient's name, age and sex, an examined region (imaged region), imaging conditions (whether a contrast medium has been used, the dose of radiation, and the like), a series number or an acquisition number when plural images are obtained in one examination, and the like. The image information is managed, for example, as XML or SGML data.

When the image information management server 5 receives a request for registration of image information from the QA-WS 2, the image information management server 5 registers the image information in the image information database 6 after appropriately converting the format of the information to a format for the database.

Further, when the image information management server 5 receives a request for retrieval from the workstation 3 for the radiology department and the workstation 4 for a clinical department through the network 9, the image information management server 5 retrieves image information registered in the image information database 6, and sends image information extracted by retrieval to the workstation 3 for the radiology department and the workstation for a clinical department that have requested the image information.

When a user, such as a doctor in charge of reading and interpreting images (hereinafter, also referred to as an image-reading doctor) and a doctor in a clinical department, performs an operation for requesting retrieval of a target image to be read or observed, the workstation 3 for the radiology department and the workstation 4 for a clinical department send a request for retrieval to the image information management server 5, and obtain necessary image information. Further, the workstation 3 for the radiology department and the workstation 4 for a clinical department display the image information on monitor screens, and execute processing for automatically detecting a lesion and the like based on a request by the user. Further, the workstation 3 for the radiology department and the workstation 4 for a clinical department send a request for retrieval of patient's information and the like by the user, such as an image-reading doctor or a doctor in a clinical department, to the information management server 10 to obtain necessary information, and display the obtained information on display screens.

The workstation 3 for the radiology department displays, on a monitor, a report generation screen for assisting a user in generation of a medical report. When a radiologist inputs text representing the content of findings based on image reading or the like, the workstation 3 for the radiology department generates a medical report in which the input information and the image that is a target of image reading (hereinafter, referred to as an image-reading target image) are recorded. When there are plural image-reading target images, a representative image that most clearly represents the findings in image reading (hereinafter, referred to as a representative image) is recorded in the medical report. The workstation 3 for the radiology department transfers the generated medical report to the medical report server 7 through the network 9, and requests the medical report server 7 to register the medical report in the medical report database 8.

The medical report server 7 is a general-purpose computer with a relatively high processing performance in which a software program that provides a function of a database management system (DataBase Management System: DBMS) has been installed. When the medical report server 7 receives a request for registration of the medical report from the workstation 3 for the radiology department, the medical report server 7 registers the medical report in the medical report database 8 after appropriately converting the format of the information to a format for the database.

For example, the medical report database 8 registers an image ID for identifying an image-reading target image or a representative image, an image-read person's ID for identifying a doctor who read the image, position information about a region of interest, findings, and information such as a degree of certainty of the findings. Further, the medical report database 8 may store an examination number and a patient's number that were obtained by referring to supplementary information of the image information during image reading. Further, the medical report database 8 may store image data representing the image-reading target image or the representative image itself. The image data representing the image-reading target image or the representative image may be reduced image data (data after thinning), and the pixel (voxel) number of which is less than that of image data registered in the image information database 6. In the present embodiment, link information (the address, the folder name, the file name and the like of image data registered in the image information database 6) is also registered in the medical report database 8. An access to image data that are registered in the image information database 6, and based on which the reduced image data are generated, is possible by the link information. Further, the image data registered in the image information database 6 may be directly copied, and the copied image data may be registered in the medical report database 8. Further, the information about the position of the region of interest may be registered, as supplementary information of the image data, in the image information database 6, instead of the medical report database 8. The medical report may be managed, for example, as XML or SGML data.

When the medical report server 7 receives a request for retrieval from the workstation 3 for the radiology department or the workstation 4 for a clinical department through the network 9, the medical report server 7 retrieves an image report registered in the medical report database 8, and sends the medical report extracted by retrieval to the workstation 3 for the radiology department or the workstation 4 for a clinical department that has requested the medical report.

The network 9 is a local area network connecting various apparatuses and devices in a hospital. When a workstation 3 for a radiology department or a workstation 4 for a clinical department is set also at a different hospital or clinic, the network 9 may be configured in such a manner to connect local area networks of hospitals or clinics to each other through the Internet or a leased line. In either case, it is desirable that the network 9 is an optical network or the like that can achieve high-speed transfer of image information.

The information management server 10 is a so-called RIS (Radiology Information System) server. The information management server 10 performs data processing to send information, such as an order of examination or diagnosis and conditions of imaging at a modality 1, to request registration or retrieval of patient's information, or the like. The order of examination or diagnosis is sent, through the network 9, from a terminal of the workstation 3 for the radiology department, which is installed in the radiology department, or a terminal of the workstation 4 for a clinical department, such as an internal medicine department or a surgery department that has requested the examination or diagnosis, to request the radiology department to perform imaging on a patient. Further, the information management server 10 manages various kinds of information, such as patient's information, clinical information, examination information, and account information, for each patient. The patient's information identifies each patient. For example, the patient's information is a patient's name, a patient's ID, or the like. Further, the patient's information may include the current address, the date of birth, the age and the sex of the patient. Further, the patient's information may include the family member composition of the patient, a medical history of the patient, whether the patient has allergy, and the like.

The clinical information is information about diagnosis performed on a patient. For example, the clinical information includes the date of diagnosis, a clinical department, a disease name, a result of diagnosis, a time period of treatment, the kind and the dose of medicine, the name of a prescription pharmacy, or the like. The time period of treatment is a period in which the patient visited a medical institution, such as a hospital, to cure a disease. In the embodiments of the present invention, the result of diagnosis includes whether definitive diagnosis has been made, and the result of the definitive diagnosis. The clinical information includes examination information. The examination information is information, such as a medical image obtained by imaging a patient to diagnose the patient. Specifically, the examination information includes the date of examination, an examination device, an examination method, an examined region and the like. The examination method refers to the direction of the patient with respect to a modality during imaging, and whether a contrast medium is used. The examined region is a target region of examination. For example, the examined region is a head region, a neck region, a chest region, an abdomen region, a pelvis region, a leg region, a region including at least two of these regions, or the like. In some cases, the account information includes, for example, an expense for a medical treatment, such as diagnosis, medicine, and examination, and whether any medical insurance is applicable.

Figure 2:
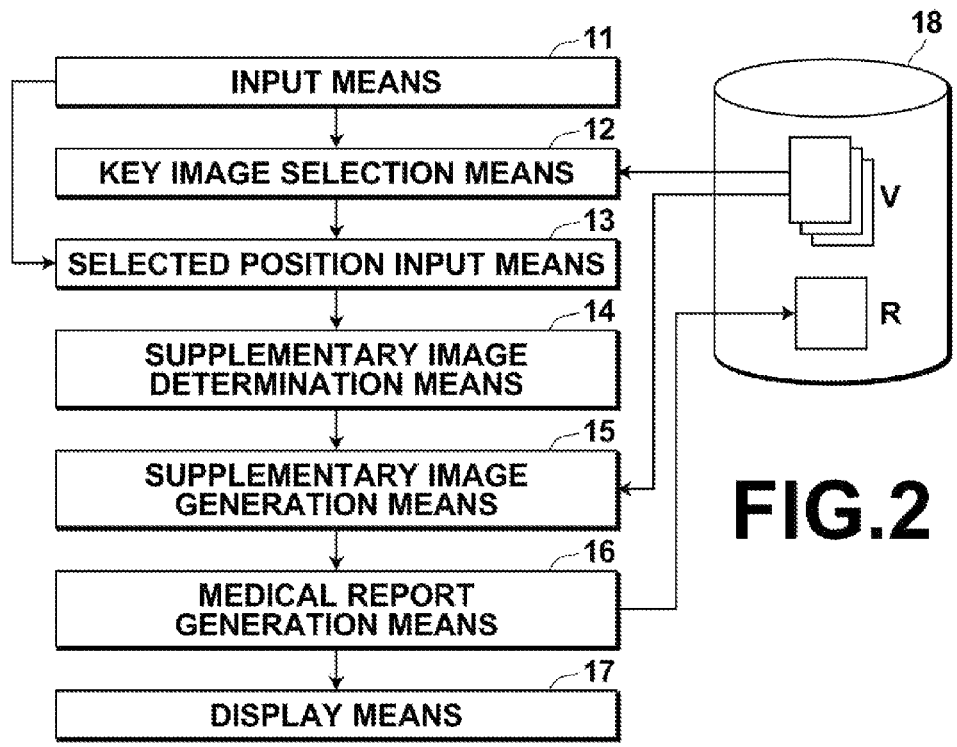
FIG. 2 is a functional block diagram of a medical report generation apparatus according to the first embodiment of the present invention.

FIG. 2 is a schematic block diagram illustrating the configuration of a medical image display system to which the medical image processing apparatus according to the first embodiment of the present invention installed in the medical information system has been applied.

In this embodiment, the workstation 3 for the radiology department (a report generation apparatus) includes an input means 11 (input device), such as a mouse and a keyboard, a storage means 18 including a storage device, such as a hard disk and a memory, and a key image selection means 12. The key image selection means 12 selects, as key image S1 representing a diagnostic characteristic feature, a slice image generated from three-dimensional medical image data V obtained by imaging a subject. Further, the workstation 3 for the radiology department includes a selected position input means 13 that inputs selected position P in the key image, and a supplementary image determination means 14. The supplementary image determination means 14 determines, as supplementary image S2, a slice image representing a cross section that includes the selected position but is different from the key image S1 by generating, based on the key image S1 and the selected position P, the slice image from the three-dimensional medical image data V. Further, the workstation 3 for the radiology department includes a medical report generation means 16 that generates medical report R including the key image S1 and information for identifying the supplementary image S2, and a supplementary image generation means 15 that generates the supplementary image S2 based on the information for identifying the supplementary image S2. Further, the workstation 3 for the radiology department includes a display means 17, such as a display, for displaying the medical report R including the information for identifying the supplementary image S2.

The key image selection means 12 selects the key image S1 that represents a diagnostic characteristic feature based on an operation by a user, such as a doctor in charge of image reading, by using the input means 11 at the input device. Further, the key image selection means 12 stores information identifying the key image S1 in the memory.

The selected position input means 13 selects selected position P representing a diagnostic characteristic feature, such as a lesion, in the key image S1 based on an operation by a user, such as a doctor in charge of image reading, by using the input means 11. The selected position P may be selected as a point. Alternatively, a straight line, a curved line, or an area having a predetermined size, such as a closed curve, may be selected as the selected position P.

The supplementary image determination means 14 obtains information identifying the selected key image S1 from the key image selection means 12, and obtains information identifying the selected position from the selected position input means 13. Further, the supplementary image determination means 14 loads, based on the information identifying the key image S1, volume data V including the key image S1 into the storage means 18, and obtains the inclination of the cross section of the key image S1 based on the loaded volume V and the key image S1. Further, the supplementary image determination means 14 determines, as the supplementary image S2, a slice image that includes the selected position P, but the inclination of which is different from the obtained inclination of the cross section of the key image S1. Further, the supplementary image determination means 14 selects an image processing parameter that is necessary to generate the supplementary image S2. In the present embodiment, when a line or an area is selected as the position, the supplementary image S2 is determined in such a manner to include a representative point, such as a center of gravity for example, included in the line or the area.

In the present embodiment, correspondence table T1, which is not illustrated, is stored in the storage means 18. The correspondence table T1 shows correspondence between the inclination of the cross section represented by the key image S1 and the inclination of the cross section represented by the supplementary image. The supplementary image determination means 14 determines the inclination of the cross section represented by the supplementary image with reference to the correspondence table T1. A user may set the correspondence table T1 in a desirable manner based on the purpose of diagnosis or the like. When the key image is an axial cross section, a supplementary image corresponding to the key image is a coronal cross section in the correspondence table T1 of the present embodiment. Further, when the key image is not an axial cross section, but a coronal cross section, a sagittal cross section or the like, a supplementary image corresponding to the key image is an axial cross section in the correspondence table T1.

The supplementary S2 may be any kind of slice image as long as the supplementary image S2 represents a cross section that is different from the key image S1. It is desirable that the key image S1 and the supplementary image S2 do not represent the same plane so that a user can refer to a sufficiently large range by using the key image S1 and the supplementary image S2. Further, it is desirable that the supplementary image represents a cross section in such a manner that the position of the cross section in the whole subject is easily recognizable even by a clinical doctor who is not used to image reading. It is desirable that the supplementary image is an image that is often used in medical treatment, such as an axial image, a coronal image, and a sagittal image, for example. Alternatively, an arbitrary slice image obtained by the MPR (Multi-Planner Reconstruction) method or the MPVR (MultiProjection Volume Reconstruction) method may be used.

The information for identifying the supplementary image includes a selected position, the inclination of the cross section represented by the supplementary image and information for identifying volume data V including key image S1. Further, the information for identifying the supplementary image includes various image processing parameters for a method for generating the supplementary image, and the like.

The supplementary image generation means 15 obtains the information for identifying the supplementary image that has been determined by the supplementary image determination means 14, and reconstructs supplementary image S2 based on volume data V by using a known method.

The medical report generation means 16 generates, based on key image S1 that has been selected by the key image selection means 12 based on an input at the input means 11 and information for identifying a supplementary image that has been determined by the supplementary image determination means 14, medical report R including the key image S1 and the information for identifying the supplementary image. The medical report R includes a comment of image reading and various kinds of information, such as finding data, which are generally provided in a medical report. FIG. 4 is a so-called image diagram illustrating the medical report R displayed on the display means 17 connected to the workstation 4 for a clinical department. As illustrated in FIG. 4, the medical report R displays image reading comment section R1, findings section R2, key image S1 and thumbnail S2a of supplementary image S2. The image reading comment section R1 displays a result of image reading by an image-reading doctor, and the findings section R2 displays finding by a clinical doctor. Instead of displaying the supplementary image S2 in the medical report R, only a supplementary image display button or the like may be displayed in the medical report R, and the supplementary image S2 may be displayed in the medical report R when an input of pressing the supplementary image display button by a user is received. In this manner, it is possible to reduce a calculation load that will be imposed by generating the supplementary image S2 every time and to satisfy a demand of users who want to display the supplementary image only if necessary.

In each process of generating the medical report, the storage means 18 appropriately stores supplementary image S2 and medical report R, which are generated by loading volume data V of a patient from the image information database 6 through the image information management server 5 and by reconstructing the volume data V, if necessary.

FIG. 3 is a flowchart illustrating a flow of medical report generation processing in the first embodiment of the present invention. With reference to FIG. 3, the flow of medical report generation processing in the first embodiment will be described.

First, a doctor in charge of image reading interprets an image based on volume data obtained by imaging a subject to be examined at a CT apparatus, and inputs, as key image S1, an image having a diagnostic characteristic feature at the workstation 3 for the radiology department. Then, the key image selection means 12 receives the input, and selects key image S1. Further, the key image selection means 12 identifies information for identifying the key image, such as a series ID of the volume data V including the key image S1 and an image ID of the key image S1, and stores the information in a memory (step S01).

Then, the image-reading doctor inputs, as selected position P, a characteristic portion in the key image S1 by using a mouse 11. The characteristic portion is a portion that the doctor has judged to be described as an image reading result. When this input is received, the selected position input means 13 inputs the coordinate of the input position, as a selected position, and stores the selected position in the memory (step S02).

The supplementary image determination means 14 obtains the coordinate of the selected position, the series ID of the volume data including the key image, and the key image ID, which have been obtained already through the processing so far. Further, the supplementary image determination means 14 identifies the inclination of a cross section represented by the key image, and determines, as supplementary image S2, a slice image that includes the coordinate of the selected position P, and the cross section of which has an inclination corresponding to the cross section represented by the key image with reference to correspondence table T1. Further, the supplementary image determination means 14 identifies information for identifying the supplementary image S2, and stores the information in the memory (step S03). Here, an axial image is selected as the key image S1, and a coronal image including the selected position P is determined as the supplementary image S2.

Next, the supplementary image generation means 15 generates, based on the information for identifying the supplementary image, the supplementary image S2 from the volume data V including the key image S1 (step S04).

The medical report generation means 16 generates medical report R including the information for identifying the generated supplementary image S2, and stores the generated medical report R in the memory (step S06). Further, when the image-reading doctor appropriately inputs a result of image reading at the input means 11, such as a keyboard, the medical report generation means 16 additionally stores the input result of image reading, as an image reading comment in the medical report R, also in the memory.

Further, the display means 17 displays the medical report R including the generated supplementary image S2 on the display 17 (step S07). As illustrated in FIG. 4, thumbnail S2a of the generated supplementary image S2 is displayed in the medical report R. Further, when the user selects the thumbnail S2a by the input means 11, the supplementary image S2 is displayed based on the information for identifying the supplementary image S2.

According to the first embodiment of the present invention, it is possible to easily generate the supplementary image S2 representing selected position P by a cross section that is different from the cross section of the key image S1. Therefore, it is possible to efficiently generate the medical report R. Further, doctors who use the medical report R for diagnosis can more easily understand the medical report R by referring to the supplementary image S2.

Meanwhile, in the method disclosed in Patent Document 1, the position of a lesion is indicated in a schematic diagram. Therefore, the position of an actual region, skeleton or the like of a patient and an anatomical position in the schematic diagram are not sufficiently matched with each other. Therefore, comparison of the positions has been difficult in some cases. However, as described in the first embodiment, a different slice image of the same patient is determined as the supplementary image in the present invention. Therefore, it is possible to observe a neighborhood of the selected position P by using the supplementary image S2 in such a manner that the anatomical position is exactly matched with the actual position. Further, in the method disclosed in Patent Document 2, there has been a problem that it is not easy to identify an image related to a key image for a user who is not used to an operation for appropriately changing an image processing parameter set and an operation for identifying an image related to a key image. However, as described in the first embodiment, a user can easily refer to the supplementary image by using the medical report R generated in the present invention even if the user does not have sufficient knowledge on an operation for generating the supplementary image.

Further, in the aforementioned embodiment, when the key image S1 is an axial image, the supplementary image determination means 14 determines a coronal image, as the supplementary image S2. Therefore, when final diagnosis is performed with reference to the result of image reading in the medical report R, a doctor in charge of a patient or the like can refer to a slice image that is often used in diagnosis, as the supplementary image. Therefore, it is possible to more easily understand the medical report R.

In the aforementioned embodiment, the supplementary image generation means 15 that generates the supplementary image S2 based on information identifying the supplementary image S2 and the display means 17 that displays medical report R including the generated supplementary image S2 are provided. Therefore, when a doctor in charge of a patient or the like refers to the medical report R, an operation for displaying the supplementary image S2 is not required, and that is convenient.

In the aforementioned embodiment, when the supplementary image S2 is determined during an operation of generating the medical report R by an image-reading doctor or the like, such as an operation of inputting an image reading comment to the medical report R, it is desirable that the supplementary image S2 is added to the medical report R even during the operation in such a manner that a user can refer to the supplementary image. That is because the image-reading doctor or the like can check whether an appropriate slice image has been determined as the supplementary image S2 while inputting the image reading comment or the like in the medical report R, and further add an image reading comment about the added supplementary image S2. The supplementary image S2 represents a cross section including selected position P, which is a characteristic portion in diagnosis. Therefore, the supplementary image S2 represents important information for diagnosis. In some cases, a user such as an image-reading doctor originally wants to include, in the medical report, plural slice images representing different cross sections including a characteristic portion for diagnosis. In such cases, if this invention is applied, it is possible to simplify the processing for generating plural slice images including a characteristic portion by inputting the characteristic portion, as a selected position, only in a slice image. Therefore, it is possible to efficiently generate the medical report.

Next, with reference to FIGS. 5 and 6, a medical report generation apparatus according to a second embodiment of the present invention will be described. FIG. 5 is a functional block diagram illustrating the medical report generation apparatus according to the second embodiment. FIG. 6 is a flowchart for explaining a flow of medical report generation processing in the second embodiment. The medical report generation apparatus according to the second embodiment differs from the medical report generation apparatus according to the first embodiment only in that a region extraction means 19 is further provided and that the supplementary image determination means 14 determines the supplementary image S2 in such a manner to change the inclination of the slice image based on a region to which the selected position P belongs. In the following descriptions, these features different from the first embodiment will be mainly described, and explanations on the common features will be omitted.

The region extraction means 19 extracts an anatomical structure from volume data V of a subject or a slice image of the subject. Here, the anatomical structure refers to a structure, such as an organ, a bone and a blood vessel, which is classified based on function and shape, for example. In the present embodiment, the region extraction means 19 includes a region extraction unit for each region to extract a region, such as an organ, a bone or a blood vessel, by using a known method.

The region extraction means 19 performs region extraction processing by storing, in advance, a result of region extraction processing on volume data V of a subject obtained by imaging in an arbitrary database. Further, when the supplementary image determination means 14 determines the supplementary image, the stored result is obtained. Alternatively, the region extraction means 19 may perform region extraction processing when the supplementary image determination means determines the supplementary image. Further, the region extraction means 19 may adopt any kind of method that can extract an anatomical structure from volume data of the subject or a slice image of the subject including the key image. For example, as the method for extracting each organ or region, techniques disclosed in Japanese Unexamined Patent Publication No. 2001-137230 and Japanese Unexamined Patent Publication No. 2008-253293 may be used for a lung field. Techniques disclosed in Japanese Unexamined Patent Publication No. 2001-283191 and U.S. Patent Application Publication No. 20020181754 may be used to extract a liver. Further, a technique disclosed in Japanese Unexamined Patent Publication No. 2008-043564 may be used for a bone, and a technique disclosed in Japanese Unexamined Patent Publication No. 2004-141612 may be used for a heart. Further, other organ recognition techniques are applicable as long as an organ or region to which the position of a selected lesion belongs can be extracted.

In correspondence table T2 used in the second embodiment, the inclination of a supplementary image corresponding to the inclination of a key image differs for each region. Here, when a region to which a selected position belongs is a vertebral column, an aorta or the like, which curves toward the front direction of the subject, if a coronal image or the like is used as the supplementary image for example, only a part of a region including the selected position is included in the supplementary image. Therefore, it is highly likely that the region including the selected region is hard to be recognized. To prevent such problems, when the region to which the selected position belongs is a region, such as a vertebral column and an aorta, which curves toward the front direction of the subject, a slice image representing a cross section including a curved line of the curved region should be determined as the supplementary image. Such a supplementary image is desirable to effectively assist a doctor or the like to recognize the shape of the region.

In view of the aforementioned points, a sagittal image, as the supplementary image, corresponds to a vertebral column and an aorta, and a coronal image, as the supplementary image, corresponds to other regions in the correspondence table T2 in the present embodiment. Further, when an organ to which the selected position belongs is a vertebral column or an aorta, the supplementary image determination means 14 determines a sagittal image including the selected position, as the supplementary image. Further, the supplementary image determination means 14 obtains supplementary image identification information for identifying the supplementary image.

With reference to FIG. 6, a flow of medical report generation processing in the second embodiment will be described. Steps S21, S22 and S25 through S28 are similar to steps S01, S02 and S04 through S06. Therefore, processing only in steps S23 and S24 will be described.

In the present embodiment, the region extraction means 19 extracts each region included in volume data V before performing report generation processing, and stores the result of extraction in the image information database 6. When the supplementary image determination means 14 obtains key image S1 and selected position P, the supplementary image determination means 14 obtains a result of region recognition from the image information database 6 through the image information management server 5 (step S23). Further, the supplementary image determination means 14 identifies a region to which the selected position belongs (step S24). With reference to correspondence table T2, the supplementary image determination means determines supplementary image S2 having the inclination corresponding to the identified region, and which includes the selected position P. Further, the supplementary image determination means 14 obtains information for identifying the supplementary image (step S25). Especially, when the extracted region is a region (an aorta or a vertebral column) that curves toward the front direction of the subject, and key image S1 is not a sagittal image, the supplementary image determination means 14 determines a sagittal image, as the supplementary image, with reference to correspondence table T2.

As described, according to the second embodiment, the supplementary image determination means 14 determines the supplementary image in such a manner that the inclination of a cross section represented by the supplementary image differs based on a selected position. Since the supplementary image is determined in such a manner that the inclination of the cross section represented by the supplementary image differs for each selected position to satisfy a user's request or the like, it is possible to determine the supplementary image having an appropriate inclination based on the position.

The region extraction means 19 for extracting a region including the input selected position from volume data V is further provided, and the supplementary image determination means 14 determines the supplementary image in such a manner that the inclination of the cross section represented by the supplementary image differs based on the extracted region. Therefore, a user can determine a slice image, as the supplementary image, having an appropriate inclination based on the region.

Further, when the extracted region is a region that curves toward the front direction of the subject, and key image S1 is not a sagittal image, the supplementary image determination means 14 determines a sagittal image, as the supplementary image S2. Therefore, it is possible to determine, as the supplementary image, an appropriate slice image having a cross section in which a region, such as a vertebral column and an aorta, which curves toward the front direction of the subject, is easily recognizable.

When the selected position belongs to a region, such as a vertebral column and an aorta, which curves toward the front direction of the subject, the supplementary image determination means 14 determines a sagittal image including the selected position as the supplementary image. Therefore, it is possible to easily observe the region, such as a vertebral column and an aorta, which curves toward the front direction of the subject, as a whole. Hence, a doctor or the like who checks the medical report by using the supplementary image can easily understand the medical report.

The present invention is not limited to the present embodiment. When the inclination of a cross section represented by a slice image in which a region is easily recognizable is further set in the correspondence table T2 based on the direction of the course of the region or the shape of the region, or a request from a doctor in each clinical department or the like, more remarkable advantageous effects are achievable.

Next, a medical report generation apparatus 4 according a third embodiment will be described. FIG. 7 is a functional block diagram of the medical report generation apparatus according to the third embodiment. FIG. 8 is a flowchart for explaining a flow of medical report generation processing according to the third embodiment. The medical report generation apparatus 4 according to the third embodiment differs from the medical generation apparatus according to the first embodiment in that an abnormal shadow extraction means 20 is further provided, and that the supplementary image determination means 14 moves selected position P into an abnormal shadow when the abnormal shadow is extracted, and identifies the supplementary image S2. In the following descriptions, these features different from the first embodiment will be mainly described, and explanations on the common features will be omitted.

The abnormal shadow extraction means 20 includes plural lesion extraction units that can extract different kinds of plural lesions. The present invention is not limited to the present embodiment, and the abnormal shadow extraction means 20 may be provided in various manners, for example, as a lesion extraction unit database connected through a network, or the like.

In the embodiments described in the specification of the present invention, all of the lesion extraction units in the abnormal shadow extraction means 20 are configured by machine learning. The abnormal shadow extraction means 20 according to the embodiments of the present invention uses Adaboosting Algorithm, and learns the feature value of each pixel (voxel) of plural positive sample images and plural negative sample images by machine learning in advance. The positive sample images used in machine learning include abnormal shadows. In the positive sample images, abnormal shadow regions have been already recognized. The negative sample images have been already recognized as images that do not include any lesions. Accordingly, evaluation function F for evaluating whether each pixel (voxel) represents an abnormal shadow is obtained by machine learning. As the feature value, feature values of plural pixels (voxels) randomly selected from each sample image should be used. The abnormal shadow extraction means 20 can extract a lesion by evaluating whether each pixel (voxel) in an arbitrary medical image represents an abnormal shadow by using the obtained evaluation function F.

The present invention is not limited to the present embodiment. Various methods may be adopted as techniques for machine learning. For example, techniques, such as neural network, support vector machine and nearest neighbor classifier, may be adopted.

Alternatively, each of the lesion extraction units in the abnormal shadow extraction means 20 in the present embodiment may adopt an abnormal shadow extraction method using various known methods other than machine learning.

The following techniques may be adopted. Specifically, techniques for detecting a lung cancer disclosed in U.S. Patent Application Publication No. 20030095692, Japanese Unexamined Patent Publication No. 2003-271924, and K. Kubota et al., "Evaluation of Computer-Aided Diagnosis system for Lung Cancer based on Helical CT images", the Institute of Electronics, Information and Communication Engineers (IEICE), IEICE Technical Report, pp. 41-46, 2001 are applicable. Further, consolidation disclosed in S. Kido et al., "Intelligent CAD for diffuse lung diseases", Grant-in-Aid for Scientific Research, granted by the Ministry of Education, Culture, Sports, Science and Technology (MEXT), Study in Specific Field "Intellectual Diagnosis Aid of Multi-Dimensional Medical Image", Proceedings of 4th Symposium, pp. 45-54, 2007 is applicable. Further, Ground-Glass Opacity (GGO) and Crazy-Paving are applicable. Further, detection techniques of diffuse lung disease, such as honeycomb-shaped shadow, pulmonary emphysema shadow and particle-shaped shadow, are applicable. Further, a technique for detecting a liver cancer disclosed in Y. Wakida et al., "Liver Cancer Detection based on a Temporal Density Feature from Abdominal Dynamic X-ray CT Images", Proceedings of Japan Society of Computer-Aided Diagnosis of Medical Images, Vol. 10, No. 1, 2007 is applicable. Further, a technique for detecting hepatocellular carcinoma, hepatic cyst, hepatic hemangioma, and bleeding in a liver region or a brain region disclosed in H. Fujita et al., "Intelligent Computer-aided Diagnosis Based on Normal Structure Recognition of Human Body", Grant-in-Aid for Scientific Research, granted by the Ministry of Education, Culture, Sports, Science and Technology (MEXT), Study in Specific Field "Intellectual Diagnosis Aid of Multi-Dimensional Medical Image", Proceedings of 4th Symposium, pp. 55-60, 2007 is applicable.

Further, a technique for detecting an abnormality of a blood vessel, as disclosed in U.S. Patent Application Publication No. 20050010100, a technique for detecting an abnormal shadow candidate disclosed in U.S. Pat. No. 5,940,527, filed by FUJIFILM Corporation, and a technique for detecting a calcification region, as disclosed in Japanese Unexamined Patent Publication No. 8 (1996)-215183, may be used.

With reference to FIG. 6, a flow of medical report generation processing in the third embodiment will be described. Steps S41, S42 and S47 through S49 are similar to steps S01, S02 and S04 through S06. Therefore, processing only in steps S43 through S46 will be described.

In the present embodiment, the abnormal shadow extraction means 20 obtains the input selected position P, and extracts an abnormal shadow in a predetermined range from the input selected position P. Further, the abnormal shadow extraction means 20 outputs a result of extraction to the supplementary image determination means 14 (step S43). When the supplementary image determination means 14 judges, based on the input result of extraction, that the abnormal shadow is present within a predetermined range from the selected position P (step S44 is YES), the supplementary image determination means 14 moves the selected position P to the center of gravity of the abnormal shadow, and stores the coordinated of the moved selected position P in the memory (step S45). In contrast, when the supplementary image determination means 14 judges, based on the input result of extraction, that the abnormal shadow is not present within the predetermined range from the selected position P (step S44 is NO), the supplementary image determination means 14 stores the coordinate of the selected position P, which is not moved, in the memory. Further, the supplementary image determination means 14 determines a supplementary image that includes the selected position P, and the inclination of which corresponds to the inclination of key image S1 with reference to correspondence table T3. Further, the supplementary image determination means 14 obtains information for identifying the supplementary image (step S46).

According to the third embodiment, the abnormal shadow extraction means 20 for extracting an abnormal shadow within a predetermined neighborhood range from a selected position is further provided. Further, the supplementary image determination means 14 moves the selected point P into the extracted abnormal shadow, and determines the supplementary image S2. Therefore, even when the abnormal shadow is extremely small, and it is difficult to input the selected position P in the abnormal shadow, it is possible to automatically move the selected position P into the abnormal shadow only by inputting the selected position P in a neighborhood of the abnormal shadow. Further, it is possible to determine the supplementary image S2 in such a manner that the moved selected position P is included in the abnormal shadow. Therefore, a user can easily input the selected position P. Further, it is possible to improve the accuracy of image reading of the supplementary image S2 and the efficiency of image reading of the supplementary image S2. Further, it is possible to prevent an erroneous input, such as an unintentional input of a selected position away from the abnormal shadow. In the third embodiment, a slice image obtained by an MPVR method may be determined as the supplementary image, depending on the kind and the size of the extracted abnormal shadow. In such a case, it is possible to refer to a supplementary image generated by using a method appropriate for image-based diagnosis in such a manner that the method is suitable for the kind and the size of the extracted abnormal shadow. Therefore, a doctor or the like who refers to the medical report R can recognize the abnormal shadow including the selected position in a more appropriate manner.

The present invention is not limited to the present embodiment. Apart or all of composition elements of the medical report generation apparatus may be composed of a workstation. Alternatively, a part or all of the composition elements of the medical report generation apparatus may be composed of at least one workstation, a server, and a storage device. Further, each device is controlled by a program for performing diagnosis-assistance processing described in the specification of the present application, and the program is installed from a recording medium, such as a CD-ROM. Alternatively, the program may be installed after being downloaded from a recording device of a server connected through a network, such as the Internet.

The embodiment of the present invention may be applied to the other embodiments without altering the gist of the invention.

What is claimed is:

1. A medical report generation apparatus comprising:
   a key image selection unit that selects, as a key image representing a diagnostic characteristic feature, a slice image generated based on three-dimensional medical image data obtained by imaging a subject;
   a selected position input unit that accepts a position input by a user on the key image and that inputs the accepted position as a selected position in the key image;
   an abnormal shadow extraction unit that extracts an abnormal shadow within a predetermined neighborhood range from the selected position;
   a supplementary image determination unit that moves the selected position into the extracted abnormal shadow based on the key image and the selected position in case that the abnormal shadow is extracted and that determines a slice image that includes the moved selected position and represents a cross section different from a cross section represented by the key image, as a supplementary image in the three-dimensional medical image data; and a medical report generation unit that generates a medical report including the key image and information for identifying the supplementary image.

2. A medical report generation apparatus, as defined in claim 1, wherein the key image is an axial image, and the supplementary image is a coronal image.

3. A medical report generation apparatus, as defined in claim 1, wherein the supplementary image determination unit determines the supplementary image in such a manner that the inclination of a cross section represented by the supplementary image differs based on the selected position.

4. A medical report generation apparatus, as defined in claim 3, the apparatus further comprising:

a region extraction unit that extracts a region including the input selected position from the three-dimensional medical image data, wherein the supplementary image determination unit determines the supplementary image in such a manner that the inclination of the cross section represented by the supplementary image differs based on the extracted region.

5. A medical report generation apparatus, as defined in claim 4, wherein the supplementary image determination unit determines a sagittal image as the supplementary image when the extracted region is curved toward the front direction of the subject and the key image is not a sagittal image.

6. A medical report generation apparatus, as defined in claim 1, wherein a multiprojection volume reconstruction image is determined as the supplementary image.

7. A medical report generation apparatus, as defined in claim 1, the apparatus further comprising:

an image generation unit that generates the supplementary image based on the information identifying the supplementary image; and a display unit that displays the medical report including the generated supplementary image.

8. A medical report generation method comprising the steps of:

selecting, as a key image representing a diagnostic characteristic feature, a slice image generated based on three-dimensional medical image data obtained by imaging a subject;

accepting a position input by a user on the key image and inputting the accepted position as a selected position in the key image;

extracting an abnormal shadow within a predetermined neighborhood range from the selected position;

moving the selected position into the extracted abnormal shadow, based on the key image and the selected position in case that the abnormal shadow is extracted and determining a slice image that includes the moved selected position and represents a cross section different from a cross section represented by the key image, as a supplementary image, in the three-dimensional medical image data; and generating a medical report including the key image and information for identifying the supplementary image.

9. A non-transitory computer-readable recording medium stored therein a program for causing a computer to function as:

a key image selection unit that selects, as a key image representing a diagnostic characteristic feature, a slice image generated based on three-dimensional medical image data obtained by imaging a subject;

a selected position input unit that accepts a position input by a user on the key image and that inputs the accepted position as a selected position in the key image;

an abnormal shadow extraction unit that extracts an abnormal shadow within a predetermined neighborhood range from the selected position;

a supplementary image determination unit that moves the selected position into the extracted abnormal shadow, based on the key image and the selected position in case that the abnormal shadow is extracted and that determines a slice image that includes the moved selected position and represents a cross section different from a cross section represented by the key image, as a supplementary image, in the three-dimensional medical image data; and a medical report generation unit that generates a medical report including the key image and information for identifying the supplementary image.

* * * * *